United States Patent
Subramaniam et al.

(10) Patent No.: US 7,365,234 B2
(45) Date of Patent: Apr. 29, 2008

(54) TUNING PRODUCT SELECTIVITY IN CATALYTIC HYDROFORMYLATION REACTIONS WITH CARBON DIOXIDE EXPANDED LIQUIDS

(75) Inventors: Bala Subramaniam, Lawrence, KS (US); Jon A. Tunge, Lawrence, KS (US); Hong Jin, Bartlesville, OK (US); Anindya Ghosh, Duncan, OK (US)

(73) Assignee: University of Kansas, Lawrence, KS (US)

( * ) Notice: Subject to any disclaimer, the term of this patent is extended or adjusted under 35 U.S.C. 154(b) by 0 days.

(21) Appl. No.: 11/687,270

(22) Filed: Mar. 16, 2007

(65) Prior Publication Data

US 2007/0219399 A1    Sep. 20, 2007

Related U.S. Application Data

(60) Provisional application No. 60/783,540, filed on Mar. 17, 2006.

(51) Int. Cl.
  *C07C 45/50* (2006.01)
(52) U.S. Cl. ....................... 568/451; 568/454
(58) Field of Classification Search ............... None
  See application file for complete search history.

(56) References Cited

U.S. PATENT DOCUMENTS 4,687,874 A    8/1987    Oswald et al.
5,780,684 A    7/1998    Drent et al.
6,740,785 B2   5/2004    Subramaniam et al.

OTHER PUBLICATIONS

Jin et al., *Homogeneous catalytic hydroformylation of 1-octene in $CO_2$-expanded solvent media*, Chem. Eng. Science, 59 4887-4893 (2004).

Webb et al., *Continuous flow homogeneous hydroformylation of alkenes using supercirtical fluids*, Green Chemistry, 7 373-379 (2005).

Jin et al., *Catalytic Hydroformylation of Higher Olefins in $CO_2$-Expanded Media: Kinetic, Mechanistic and Economic Aspects*, Annual AIChE meeting in Cincinnati OH, Oct. 31, 2005 [Abstract only].

Meehan et al., "Continuous, Selective Hydroformylation in Supercriticial Carbon Dioxide Using an Immobilized Homogeneous Catalyst", 2000, Chem. Commun., pp. 1497-1498.

Shibahara et al., "Solvent-Free Asymmetric Olefin Hydroformulation Catalyzed by Highly Cross-Linked Polystyrene-Supported (R,S)-BINAPHOS-Rh(I) Complex", 2003, J. Am. Chem. Soc., vol. 125, pp. 8555-8560.

*Primary Examiner*—Sikarl A. Witherspoon
(74) *Attorney, Agent, or Firm*—Stinson Morrison Hecker, LLP (57) ABSTRACT

An improved hydroformylation process is provided, which comprises reacting an olefin with CO and $H_2$ in the presence of a hydroformylation catalyst in a liquid that has been volumetrically expanded with a compressed gas, such as supercritical carbon dioxide.

40 Claims, 5 Drawing Sheets

TUNING PRODUCT SELECTIVITY IN CATALYTIC HYDROFORMYLATION REACTIONS WITH CARBON DIOXIDE EXPANDED LIQUIDS

CROSS-REFERENCE TO RELATED APPLICATIONS

This application is based on and claims priority to U.S. Provisional Patent Application Ser. No. 60/783,540, filed on Mar. 17, 2006, which is incorporated herein by reference.

STATEMENT REGARDING FEDERALLY SPONSORED RESEARCH OR DEVELOPMENT

The present invention was sponsored in part by National Science Foundation Grant No. EEC-0310689 and the government may have certain rights in the invention.

BACKGROUND OF THE INVENTION

The hydroformylation reaction is well known in the art as a catalytic method for the conversion of an olefin into an aldehyde product having one carbon more than the starting olefin by the addition of one molecule each of hydrogen and carbon monoxide to the carbon-carbon double bond. If the organic substrate contains more than one carbon-carbon double bond, more than one formyl group can be added to the substrate, thereby increasing the number of carbon atoms contained in the product molecule by more than one.

Industrial processes for the catalytic hydroformylation of higher olefins (i.e., those olefins having more than five carbons) face several challenges, including efficient catalyst recovery/recycle and the limited solubilities of the gaseous reactants ($H_2$ and CO) in the liquid reaction phase. See Frohling et al., *Applied homogeneous catalysis with organometallic compounds*, VCH, Weinheim, Germany, 27-104 (1996). The commercial catalysts used in the lower olefin processes, mostly rhodium-based, are not applied in higher olefin hydroformylation because of their instability at the temperatures required for product separation/distillation. Hence, while the less expensive cobalt-based catalysts are used, harsher conditions (140-200° C., 5-30 MPa) are often employed to activate and stabilize the catalysts. In addition, the catalyst recovery typically involves significant quantities of solvents, acids, and bases in a series of many operating units. See Garton et al., PCT International Application, WO 2003/082789. Thus, an engineered system is desired to realize process intensification at milder conditions with a highly active catalyst that requires a relatively simpler and environmentally friendlier catalyst recovery method.

Several approaches for catalyst recovery have been reported in literature. The first approach involves immobilizing homogeneous rhodium ("Rh") catalysts on various supports, i.e., the silicate MCM-41 (see Marteel et al., *Supported platinum/tin complexes as catalysts for hydroformylation of 1-hexene in supercritical carbon dioxide*, Catalysis Communications, 4 309-314 (2003)), zeolites (see Mukhopadhyay et al., *Encapsulated HRh(CO)—(PPh$_3$)$_3$ in microporous and mesoporous supports: novel heterogeneous catalysts for hydroformylation*, Chemical Materials, 15 1766-1777 (2003)), nanotubes (see Yoon et al., *Rh-based olefin hydroformylation catalysts and the change of their catalytic activity depending on the size of immobilizing supporters*, Inorganica Chimica Acta., 345 228-234 (2003)), supported aqueous phase catalysis ("SAPC") (see Dessoudeix et al., *Apatitic tricalcium phosphate as novel smart solids for supported aqueous phase catalysis (SAPC)*, Advanced Synthetic Catalysis, 344 406-412 (2002)), and polymers (see Lu et al., *Hydroformylation reactions with recyclable rhodiumcomplexed dendrimers on a resin*, Journal of American Chemical Society, 125 13126-13131 (2003) and Lopez et al., *Evaluation of polymer-supported rhodium catalysts in 1-octene hydroformylation in supercritical carbon dioxide*, Industrial & Engineering Chemistry Research, 42 3893-3899 (2003)).

The second approach involves biphasic media, such as water/organic (see Peng et al., *Aqueous biphasic hydroformylation of higher olefins catalyzed by rhodium complexes with amphiphilic ligands of sulfonated triphenylphosphine analog*, Catalysis Letters, 88 219-225 (2003)), water/$CO_2$ (see Haumann et al., *Hydroformylation in microemulsions: conversion of an internal long chain alkene into a linear aldehyde using a water soluble cobalt catalyst*, Catalysis Today, 79-80 43-49 (2003); McCarthy et al., *Catalysis in inverted supercritical $CO_2$/aqueous biphasic media*, Green Chemistry, 4(5) 501-504 (2002)), and room temperature ionic liquid/$CO_2$ (see Webb, *Continuous flow hydroformylation of alkenes in supercritical fluid-ionic liquid biphasic systems*, Journal of American Chemical Society, 125 15577-15588 (2003)), wherein the catalyst is sequestered in either the water or the ionic liquid phases whereas the product preferentially separates into the organic phase or the $CO_2$ phase.

The third approach involves employing a "phase transition switch" whereby reactions are performed homogeneously, following which the catalysts are recovered from the product stream via phase transition triggered by a change in either the system temperature (see Horváth et al., *Facile catalyst separation without water: fluorous biphasic hydroformylation of olefins*, Science, 266 (5182) 72-75 (1994); Zheng et al., *Thermoregulated phase transfer ligands and catalysis. III. Aqueous/organic two-phase hydroformylation of higher olefins by thermoregulated phase-transfer catalysis*, Catalysis Today, 44 175-182 (1998)) or pressure (see Koch et al., *Rhodium-catalyzed hydroformylation in supercritical carbon dioxide*, Journal of American Chemical Society, 120 13398-13404 (1998); Palo et al., *Effect of ligand modification on rhodium-catalyzed homogeneous hydroformylation in supercritical carbon dioxide*, Organometallics, 19 81-86 (2000)).

The use of $CO_2$-expanded liquids ("CXLs") as reaction media has received increased attention by the present inventors. CXLs are a continuum of compressible media generated when various amounts of dense phase carbon dioxide are added to an organic solvent. CXLs offer both reaction and environmental benefits. Near-critical carbon dioxide possesses highly tunable transport properties ranging from gas-like diffusivities to liquid-like viscosities. See Subramaniam et al., *Reaction in supercritical fluids—a review*, Industrial & Engineering Chemistry Process Design and Development, 25 1-12 (1986). The presence of dense $CO_2$ imparts similar tunability to CXLs as well. The solubilities of many gaseous reagents (i.e., $O_2$, $H_2$) in CXLs are enhanced several-fold relative to the neat liquid phase (i.e., those without any CXLs). See Hert et al., *Enhancement of oxygen and methane solubility in 1-hexyl-3-methylimidazolium bis (trifluoromethylsul-fonyl)imide using carbon dioxide*, Chemical Communications, 2603-2605 (2005); Wei et al., *Autoxidation of 2,6-di-tertbutyl-phenol with cobalt Schiff base catalysts by oxygen in $CO_2$-expanded liquids*, Green Chemistry, 6 387-393 (2004); Solinas et al., *Enantioselective hydrogenation of imines in ionic liquid/carbon dioxide media*, Journal of American Chemical Society, 126 16142-

16147 (2004); Bezanehtak et al., *Vapor-liquid equilibrium for the carbon dioxide+hydrogen+methanol ternary system*, Journal of Chemical Engineering Data, 49 430-434 (2004); Xie et al., *Bubble and dew point measurements of the ternary system carbon dioxide+methanol+hydrogen at 313.2 K*, Journal of Chemical Engineering Data, 50 780-783 (2005). Although most transition metal complexes are only sparingly soluble in supercritical $CO_2$ ($scCO_2$), the presence of an appropriate amount of the organic liquid in CXLs ensures adequate solubilities of transition metal complexes in a CXL phase for performing homogeneous catalysis. Further, such solubilities are realized at pressures an order of magnitude lower than those required in $scCO_2$ medium for solubilizing Rh catalyst complexes with fluorinated ligands. See Palo et al., *Effect of ligand modification on rhodium-catalyzed homogeneous hydroformylation in supercritical carbon dioxide*, Organometallics, 19 81-86 (2000).

Recently, the present inventors reported the homogeneous catalytic hydroformylation of 1-octene in $CO_2$-expanded acetone with an unmodified rhodium catalyst. See Jin et al. *Homogeneous catalytic hydroformylation of 1-octene in $CO_2$-expanded solvent media*, Chemical Engineering Science, 59 4887-4893 (2004). At 30 and 60° C., the turnover frequencies ("TOFs") in $CO_2$-expanded acetone were up to four-fold greater than those obtained in either neat acetone (a polar solvent) or compressed $CO_2$. The enhanced rates in CXLs were realized at significant solvent replacement (up to 80% by volume) and at mild operating pressures (less than 12 MPa). Although the hydroformylation rates were enhanced, the regioselectivity towards linear and branched aldehydes (n/i ratio) remained unaffected by the change in either the acetone/$CO_2$ ratio or the temperature.

In industrial practice, the ability to tune the product regioselectivity is of interest. In the case of industrial linear olefin hydroformylation, the linear aldehyde is the desired product. It is shown in the present invention, that when the properties of the reaction mixture (containing an excess of non-polar 1-octene as the solvent) are tuned by $CO_2$ addition, the regioselectivity may be tuned. At increased $CO_2$ content in the liquid phase reaction mixture, the regioselectivity is favored toward the linear product and vice-versa. With change in $CO_2$ content, the syngas solubilities in and the dielectric constant of the resulting reaction mixture may be continuously varied, influencing the product selectivity. This aspect was not observed in the previous published literature which described experiments performed with a polar solvent such as acetone mixed with $CO_2$.

BRIEF SUMMARY OF THE INVENTION

The invention provides for an improved hydroformylation process comprising reacting an olefin with CO and $H_2$ in the presence of a hydroformylation catalyst in a liquid that has been volumetrically expanded with a compressed gas, such as supercritical or subcritical carbon dioxide. Surprisingly, altering the amount of the compressed gas in the liquid phase alters the chemoselectivity of the products. In addition, varying the content of the compressed gas in the liquid alters the regioselectivity of the products. The addition of the increasing amounts of the compressed gas surprisingly improves the ratio of linear to branched aldehydes during the hydroformylation process, and vice-versa.

Because n-aldehydes are generally of significantly greater industrial importance than the isoaldehydes during linear olefin hydroformylation, it is an aim to optimize the hydroformylation catalysts and conditions in order to achieve the greatest possible n-selectivity, i.e. the highest possible ratio of n-aldehyde to isoaldehyde in the product aldehydes.

Thus, in one aspect, the present invention is directed to a method for obtaining a target regioselectivity of linear aldehydes over branched aldehydes during hydroformylation of an olefin comprising the steps of: (1) reacting an olefin substrate with CO and $H_2$ in the presence of a hydroformylation catalyst in a liquid that has been volumetrically expanded with a compressed gas, and (2) varying the content of the compressed gas in the liquid in order to obtain said desired target regioselectivity. In one aspect, the target regioselectivity is preferably greater than about 10, 12, or 14.

In still another aspect, the present invention is directed to a method for obtaining a target chemoselectivity of aldehydes during hydroformylation of an olefin comprising the steps of: (1) reacting an olefin substrate with CO and $H_2$ in the presence of a hydroformylation catalyst in a liquid that has been volumetrically expanded with a compressed gas, and (2) varying the content of the compressed gas in the liquid in order to obtain said desired target chemoselectivity. The target chemoselectivity is preferably greater than about 90%, 95%, or 99%.

In one aspect, the compressed gas preferably has a volume fraction in the liquid phase between 10% and 90%. In another aspect, more than 30%, 40%, 50%, or 60% of the liquid phase volume is replaced with the compressed gas.

In one aspect, the olefin is a higher olefin, and may be linear, branched, with an internal or terminal double bond (or a combination thereof).

In another aspect, the hydroformylation catalyst is a rhodium catalyst, with Rh(acac)(CO)$_2$; Rh(acac)[P(OPh)$_3$]$_2$; Rh(acac)(CO)[P(OAr)$_3$]; and a complex formed of Rh(acac)(CO)$_2$ and a phosphorous-containing ligand being exemplary. In an exemplary aspect, the ligand to rhodium molar ratio ranges between 1 and 270.

In still another aspect, the reaction mixture is formed in a polar organic solvent, such as acetone. In yet another aspect, the reaction mixture uses the olefin substrate, a non-polar substance, as the liquid phase. Thus, the methods of the present invention are employed in both the both in the presence and absence of added organic solvents, such as acetone, with the resulting chemo and regioselectivities being influenced by the polar or non-polar nature of the reaction mixture In a further aspect, the enhanced rates and selectivities were realized in CXLs at a 50% reduction in the organic solvent usage.

In still another aspect, the reaction occurs at relatively mild temperatures and pressures. Typical temperatures range between 30° C. and 90° C., and typical pressures are less than 12 MPa, with pressures between about 4 to 6 MPa being exemplary.

In still another aspect, the process also results in an improved turnover frequency. In one aspect, the observed TOF was about 300 1/hour. In experiments performed without added solvent, a TOF maximum was observed at an optimum $CO_2$ content in the liquid phase.

In yet a further aspect, the process also results in improved chemoselectivity ($S_a$). In an exemplary embodiment with Rh(acac)(CO)$_2$ modified by biphephos ligand as the catalyst, the selectivity to aldehyde products was improved from approximately 70% in neat solvent to nearly 95% in CXL media.

Although not intended to be bound by any particular theory, the enhanced rates and selectivity are attributed to a combination of optimal syngas availability in and the tuned properties (such as dielectric constant) of the CXL phase.

In still another aspect, because an excess amount of $CO_2$ addition causes the transition metal complex catalyst to precipitate from the CXL phase, the present invention also contemplates the separation of the catalyst post-reaction. Indeed, catalysts may be designed to take advantage of this highly tunable solubility for recovery and recycle. For example, catalysts may be supported on soluble polymers whose solubilities in the reaction mixture are highly dependent on the dielectric constant of the reaction mixture. Since the polarity of the CXL phase is easily tuned by $CO_2$ addition, the solubility of the catalyst may likewise be tuned to stay in solution during the reaction phase and precipitate upon $CO_2$ addition following reaction. It should be understood that the polarity switching may be performed with other solvents as well. The significant replacement of volatile organic solvents ("VOCs") by dense $CO_2$ in CXLs results in improved process safety and less exposure to hazardous materials. In addition, the unique heat capacities of near-critical $CO_2$ may be exploited to effectively curtail the temperature rise of a highly exothermic reaction and thereby to prevent thermal runaway. See Jin et al., *Exothermic oxidations in supercritical $CO_2$: effects of pressure-tunable heat capacity on adiabatic temperature rise and parametric sensitivity*, Chemical Engineering Science, 58: 1897-1901 (2003).

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

As used herein, the term "carbon dioxide expanded liquids" or "CXLs" refer to a continuum of compressible media generated when a dense phase carbon dioxide is added to an organic liquid media. Pressurized subcritical or supercritical carbon dioxide is usually the gas of choice.

As used herein, the term "higher olefins" refers to olefins having more than five carbons in the chain.

As used herein, the term "internal" olefins are accordingly olefins whose double bond is, unlike alpha-olefins, not terminal but located in the interior of the olefin molecule.

As used herein, the term "turnover frequency" or "TOF" refers to a moles of substrate (e.g. 1-octene) converted to all products per mole of catalyst per hour during fixed-time batch runs.

As used herein, the term "chemoselectivity" or "$S_a$" refers to the moles of aldehydes or the octene isomers formed relative to the moles of substrate (e.g., octene) converted during the hydroformylation process.

As used herein, the term "regioselectivity" or "n/i" refers to the ratio of linear to branched aldehydes in the product.

The invention provides for an improved hydroformylation process comprising reacting an olefin with CO and $H_2$ in the presence of a hydroformylation catalyst in a liquid that has been volumetrically expanded with a compressed gas, such as supercritical or subcritical carbon dioxide. The addition of the increasing amounts of the compressed gas surprisingly improves the ratio of linear to branched aldehydes during the 1-octene hydroformylation process.

The expanding gas is generally selected from the group consisting of carbon dioxide, $N_2O$, Xenon, and $SF_6$, although for reasons of cost and ease of use, pressurized subcritical or supercritical carbon dioxide is usually the gas of choice. The expanding gas is present in the reaction mixture at a level below that which will cause the catalyst to precipitate; that is, the catalyst is usually least soluble component of the reaction mixture, and for good results, it should remain dispersed. Therefore, the expanding gas is introduced at levels which will maintain catalyst suspension. These levels of course vary depending upon the components of the reaction mixture, and especially the catalyst. It is therefore usually necessary to preliminarily determine the extent of expanding gas supplementation which can be accommodated with each individual reaction mixture. See Subramaniam, U.S. Pat. No. 6,740,785, which is incorporated by reference.

The hydroformylation is carried out in a homogeneous reaction system. The term homogeneous reaction system generally refers to a homogeneous solution composed essentially of $CO_2$-expanded solvent, catalyst, syngas, olefinically unsaturated compound, and reaction product.

The amount of rhodium compound is not specially limited, but is optionally selected so that favorable results can be obtained with respect to catalyst activity and economy. In general, the concentration of rhodium in the reaction medium is between 10 and 10,000 ppm and more preferably between 50-500 ppm, calculated as the free metal.

The volume ratio of carbon monoxide to hydrogen in the synthesis gas is generally in the range from 10 to 1 and 1 to 10, preferably between 6 to 1 to 1 to 6, and most preferably 2:1 to 1:2, in particular 1:1. The synthesis gas is advantageously used in excess, for example in an amount up to three times the stoichiometric amount.

The olefin substrates in the present invention may be any organic compound having at least one ethylenically unsaturated functional group (i.e., a carbon-carbon double bond) and may be, for example, an aromatic, aliphatic, mixed aromatic-aliphatic (e.g., aralkyl), cyclic, branched or straight chain olefin. Preferred olefins are $C_2$ to $C_{20}$ olefins, and most preferred are "higher olefin" which refers to a compound containing more than 5 carbon atoms. More than one carbon-carbon double bond may be present in the olefin, and thus, dienes, trienes, and other polyunsaturated substrates thus may be used. The olefin may optionally contain substituents other than hydrocarbon substituents such as halide, carboxylic acid, ether, hydroxy, thiol, nitro, cyano, ketone, ester, anhydride, amino, and the like.

Exemplary olefins suitable in the process of the present invention include ethylene, propylene, butenes, butadiene, pentenes, isoprene, 1-hexene, 3-hexene, 1-heptene, 1-octene, diisobutylene, 1-nonene, 1-tetradecene, pentamyrcene, camphene, 1-undecene, 1-dodecene, 1-tridecene, 1-tetradecene, 1-pentadecene, 1-hexadecene, 1-heptadecene decene, 1-nonadecene, 1-eicosene, the trimers and tetramers of propylene, polybutadiene, polyisoprene, cyclopentene, cyclohexene, cycloheptene, cyclooctene, cyclooctadiene, cyclododecene, cyclododecatriene, dicyclopentadiene, methylenecyclopropane, methylenecyclopentane, methylenecyclohexane, vinylcyclohexane, vinyl cyclohexene, methallyl ketone, allyl chloride, allyl bromide, acrylic acid, methacrylic acid, crotonic acid, vinyl acetic acid, crotyl chloride, methallyl chloride, the dichlorobutenes, allyl alcohol, allyl carbonate, allyl acetate, alkyl acrylates and methacrylates, diallyl maleate, diallyl phthalate, unsaturated triglycerides such as soybean oil, and unsaturated fatty acids, such as oleic acid, linolenic acid, linoleic acid, erucic acid, palmitoleic acid, and ricinoleic acid and their esters (including mono-, di-, and triglyceride esters), and alkenyl aromatic compounds such as styrene, alpha-methyl styrene, beta-methyl styrene, divinyl benzene, 1,2-dihydronaphthalene, indene, stilbene, cinnamyl alcohol, 2-methyl-1-phenyl-1-propene, 2-methyl-3-phenyl-2-propen-1-ol, cinnamyl acetate, cinnamyl bromide, cinnamyl chloride, 4-stilbenemethanol, ar-methyl styrene, ar-ethyl styrene, ar-tert-butyl styrene, archlorostyrene, 1,1-diphenylethylene, vinyl benzyl chloride, vinyl naphthalene, vinyl benzoic acid, ar-acetoxy styrene, ar-hydroxy styrene (i.e., vinyl phenol), 2- or 3-methyl indene, 2,4,6-trimethylstyrene, 1-phenyl-1-cyclohexene, 1,3-diisopropenyl benzene, vinyl anthracene, vinyl anisole, and the like.

In an exemplary aspect, the olefin is a fatty compound, for example, mono- and poly-unsaturated free fatty acids, fatty esters, triglyceride oils, or other fatty-derived materials. Suitable olefins are described in Frankel, U.S. Pat. No. 4,083,816, which is incorporated by reference.

Of these, linear higher olefins are most preferred. The olefin is preferably present in about 0.1 to 99.99 mol % of the reaction mixture. It will be appreciated to those skilled in the art that the olefin concentration (i.e., availability) in the liquid phase, where the reaction occurs, is most important, and for low boiling light olefins this is dictated by the operating pressure and temperature.

The hydroformylation catalyst may be any transition metal capable of carrying out catalytic transformations and may additionally contain labile ligands which are either displaced during the catalytic reaction, or take an active part in the catalytic transformation. Any of the transition metals may be considered in this regard. The preferred metals are those comprising Group VIII of the Periodic Table. The preferred metals for hydroformylation are rhodium, cobalt, iridium, ruthenium, palladium, and platinum. The Group VIII metal is preferably rhodium.

Group VIII catalysts suitable for hydroformylation, can be prepared or generated according to techniques well known in the art, as described, for example, in WO 95 30680, U.S. Pat. No. 3,907,847; and J. Amer. Chem. Soc., 115, 2066 (1993). Suitable Group VIII metal compounds are hydrides, halides, organic acid salts, acetylacetonates, inorganic acid salts, oxides, carbonyl compounds and amine compounds of these metals. Preferred salts include, for example, rhodium salts such as rhodium acetate, rhodium chloride or rhodium nitrate, rhodium complexes such as rhodium acetylacetonate and/or rhodium carbonyl compounds. In addition, the catalyst may be achiral or chiral.

The ligands can be monodentate or polydentate, and in the case of chiral ligands, either the racemate or one enantiomer or diastereomer can be used. Preferred ligands are ligands which contain nitrogen, phosphorus, arsenic, or antimony as donor atoms; particular preference is given to phosphorus-containing ligands, such as phosphines, phosphine oxides, phosphinanes, phosphinines, phosphinites, phosphites, and phosphonites.

Examples of phosphines are triphenylphosphine, tris(p-tolyl)phosphine, tris(m-tolyl)phosphine, tris(o-tolyl)phosphine, tris(p-methoxyphenyl)phosphine, tris(p-fluorophenyl)phosphine, tris(p-chlorophenyl)phosphine, tris(p-dimethylaminophenyl)phosphine, ethyldiphenylphosphine, propyldiphenylphosphine, t-butyldiphenylphosphine, n-butyldiphenylphosphine, n-hexyldiphenylphosphine, c-hexyldiphenylphosphine, dicyclohexylphenylphosphine, tricyclohexylphosphine, tricyclopentylphosphine, triethylphosphine, tri(1-naphthyl)phosphine, tri-2-furylphosphine, tribenzylphosphine, benzyldiphenylphosphine, tri-n-butylphosphine, tri-i-butylphosphine, tri-t-butylphosphine, bis(2-methoxyphenyl)phenylphosphine, neomenthyldiphenylphosphine, 1,2-bis(dicyclohexylphosphino)ethane, bis(dicyclohexylphosphino)methane, 1,2-bis(diethylphosphino)ethane, 1,2-bis(2,5-diethylphospholano) benzene [Et-DUPHOS], 1,2-bis(2,5-diethylphospholano) ethane [Et-BPE], 1,2-bis(dimethylphosphino)ethane, bis (dimethylphosphino)methane, 1,2-bis(2,5-dimethylphospholano)benzene [Me-DUPHOS], 1,2-bis(2,5-dimethylphospholano)ethane [Me-BPE], 1,2-bis (diphenylphosphino)benzene, 2,3-bis(diphenylphosphino) bicyclo[2.2.1]hept-5-ene [NORPHOS], 2,2'-bis (diphenylphosphino)-1,1'-binaphthyl [BINAP], 2,2'-bis (diphenylphosphino)-1,1'-biphenyl [BISBI], 2,3-bis (diphenylphosphino)butane, 1,4-bis(diphenylphosphino) butane, 1,2-bis(diphenylphosphino)ethane, bis(2-diphenylphosphinoethyl)phenylphosphine, 1,1'-bis (diphenylphosphino)ferrocene, bis(diphenylphosphino) methane, 1,2-bis(diphenylphosphino)propane, 2,2'-bis(di-p-tolylphosphino)-1,1'-binaphthyl, O-isopropylidene-2,3-dihydroxy-1,4-bis(diphenylphosphino)butane [DIOP], 2-(diphenylphosphino)-2'-methoxy-1,1'-binaphthyl, 1-(2-diphenylphosphino-1-naphthyl)isoquinoline, 1,1,1-tris (diphenylphosphino)ethane, and/or tris(hydroxypropyl) phosphine.

Examples of phosphinanes include 2,6-bis(2,4-dimethylphenyl)-1-octyl-4-phenylphosphinane, 1-octyl-2,4,6-triphenylphosphinane and further ligands described in WO 02/00669.

Examples of phosphinines include 2,6-dimethyl-4-phenylphosphinine, 2,6-bis(2,4-dimethylphenyl)-4-phenylphosphinine and also further ligands described in WO 00/55164.

Examples of phosphites are trimethyl phosphite, triethyl phosphite, tri-n-propyl phosphite, tri-i-propyl phosphite, tri-n-butyl phosphite, tri-i-butyl phosphite, tri-t-butyl phosphite, tris(2-ethylhexyl)phosphite, triphenyl phosphite, tris (2,4-di-t-butylphenyl)phosphite, tris(2-t-butyl-4-methoxyphenyl)phosphite, tris(2-t-butyl-4-methylphenyl) phosphite, tris(p-cresyl)phosphite. Further examples are sterically hindered phosphite ligands as are described, inter alia, in EP 155 508; U.S. Pat. No. 4,668,651; U.S. Pat. No. 4,748,261; U.S. Pat. No. 4,769,498; U.S. Pat. No. 4,774,361;

U.S. Pat. No. 4,835,299; U.S. Pat. No. 4,885,401; U.S. Pat. No. 5,059,710; U.S. Pat. No. 5,113,022; U.S. Pat. No. 5,179,055; U.S. Pat. No. 5,260,491; U.S. Pat. No. 5,264,616; U.S. Pat. No. 5,288,918; U.S. Pat. No. 5,360,938; EP 472 071; EP 518 241; and WO 97/20795. Triphenyl phosphites which are substituted by 1 or 2 isopropyl and/or tert-butyl groups on the phenyl rings, preferably in the ortho position relative to the phosphite ester group, are preferably used. Bisphosphite ligands which are described, inter alia, in EP 1 099 677; EP 1 099 678; WO 02.00670; JP 10279587; EP 472017; WO 01/21627; WO 97/40001; WO 97/40002; U.S. Pat. No. 4,769,498; EP 213639; and EP 214622, are particularly preferably used.

Customary phosphinite ligands are described, inter alia, in U.S. Pat. No. 5,710,344; WO 95 06627; U.S. Pat. No. 5,360,938; and JP 07082281. Examples are diphenyl(phenoxy)phosphine and its derivatives in which all or some of the hydrogen atoms are replaced by alkyl or aryl radicals or halogen atoms, diphenyl(methoxy)phosphine, diphenyl (ethoxy)phosphine, etc.

Examples of phosphonites are methyldiethoxyphosphine, phenyldimethoxyphosphine, phenyldiphenoxyphosphine, 6-phenoxy-6H-dibenz[c,e] [1,2]oxaphosphorin and their derivatives in which all or some of the hydrogen atoms are replaced by alkyl or aryl radicals or halogen atoms and ligands as described in WO 98/43935; JP 09-268152; and DE 198 10 794, and in the German patent applications DE 199 54 721 and DE 199 54 510.

Figure 1:
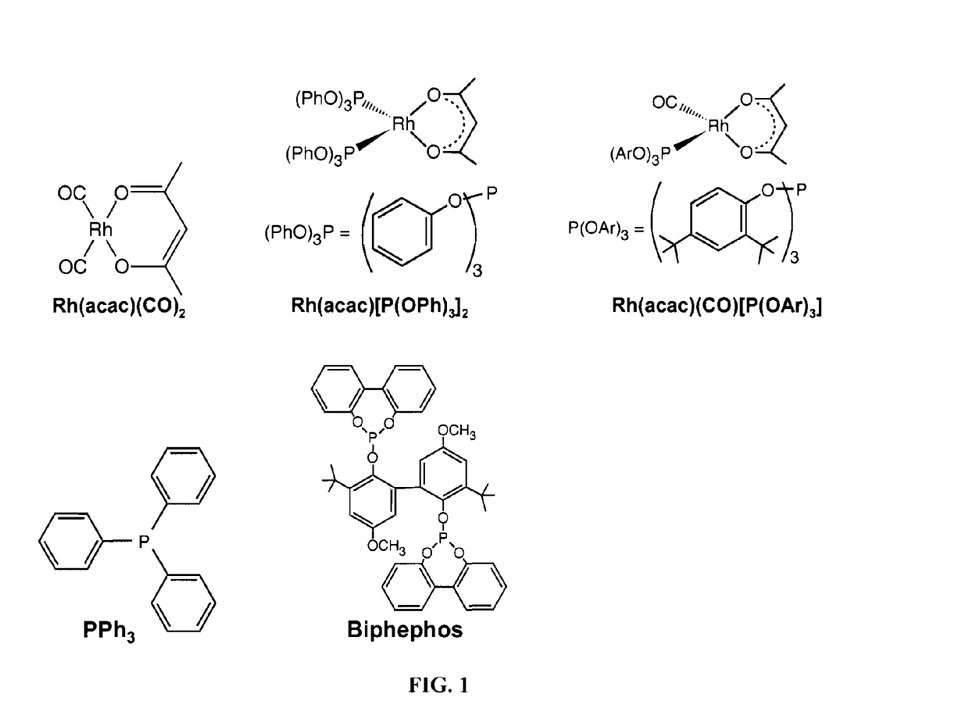
FIG. 1 shows the chemical structures of the rhodium catalysts and ligands investigated in the examples.

Other examples of rhodium catalysts include $RhCl_3$, $Rh(NO_3)_3$, $Rh(OAc)_3$, $Rh_2O_3$, $Rh(acac)(CO)_2$, $[Rh(OAc)(COD)]_2$, $Rh_4(CO)_{12}$, $Rh_6(CO)_{16}$, $RhH(CO)(Ph_3P)_3$, $[Rh(OAc)(CO)_2]$, $[RhCl(COD)]_2$, $Rh(CO)_2(acac)$, $Rh(CO)_2(C_4H_9COCHCO-t-C_4H_9)$, $Rh_2O_3$, $Rh(O_2CCH_3)_2$, and Rh(2-ethylhexanoate), wherein "acac" is an acetylacetonate group; "OAc" is an acetyl group; "COD" is 1,5-cyclooctadiene; "Ph" is a phenyl group, and "OAr" is 2,4-di-tertbutylphenyl. However, it should be noted that the Group VIII metal compounds are not necessarily limited to the above listed compounds. Rhodium compounds that contain ligands which can be displaced by the multidentate phosphites are a preferred source of rhodium. The structures of the exemplary catalysts investigated, in the examples including the unmodified $Rh(acac)(CO)_2$ and those modified by various phosphorous ligands, are summarized in FIG. 1.

The rhodium concentration in the liquid reaction mixture is generally from 10 to 500 ppm by weight, preferably from 30 to 350 ppm by weight and particularly preferably from 50 to 300 ppm by weight.

The hydroformylation process of the present invention can advantageously be carried out in the presence of solvents. In general, the polarity of the solvent will impact the regioselectivity, with non-polar solvents generally yielding higher n/i ratios. Adding a compressed gas such as $CO_2$ to the solvent allows for the continuous tenability of the polarity of the solvent system towards a more non-polar system. As solvents, preference is given to using the aldehydes which are formed in the hydroformylation of the respective olefins and also their higher-boiling downstream reaction products, i.e. the products of aldol condensation. Solvents which are likewise suitable are the olefins themselves, aromatics such as toluene and xylenes, hydrocarbons or mixtures of hydrocarbons, which can also serve for diluting the above-mentioned aldehydes and the downstream products of the aldehydes. Further possible solvents are esters of aliphatic carboxylic acids with alkanols, for example ethyl acetate or Texanol®, ethers such as tert-butyl methyl ether and tetrahydrofuran. Is also possible to use non-polar solvents, e.g. alcohols such as methanol, ethanol, n-propanol, isopropanol, n-butanol, isobutanol, ketones such as acetone, and methyl ethyl ketone etc. "Ionic liquids" can also be used as solvents. These are liquid salts, for example N,N'-dialkylimidazolium salts such as N-butyl-N'-methylimidazolium salts, tetraalkylammonium salts such as tetra-n-butylammonium salts, N-alkylpyridinium salts such as n-butylpyridinium salts, tetraalkylphosphonium salts such as trishexyl(tetradecyl)phosphonium salts, e.g. the tetrafluoroborates, acetates, tetrachloroaluminates, hexafluorophosphates, chlorides, and tosylates.

The invention will be illustrated by the following non-limiting examples. In the following examples, the materials included HPLC-grade 1-octene, acetone, and 2-propanol procured from Aldrich Chemical Co., distilled using Schlenk line to remove water, air, and peroxide impurities, and stored under nitrogen before usage. The unmodified rhodium catalyst, $Rh(acac)(CO)_2$ and triphenylphosphine ($PPh_3$) ligand were procured from Johnson Matthey and Strem Chemicals Inc, respectively. Two other rhodium catalysts, $Rh(acac)[P(OPh)_3]_2$ and $Rh(acac)(CO)[P(OAr)_3]$ and one bidentate ligand (biphephos) were synthesized following reported procedures. See Jongsma et al., *Fine tuning of bulky-phosphite modified rhodium catalysts by binding them to copolymers*, Journal of Molecular Catalysis, 83 17-35 (1993); Billig et al., U.S. Pat. Nos. 4,668,651 (1987) and 4,769,498 (1988). All catalysts and ligands were stored under nitrogen before usage. Coolant-grade liquid $CO_2$ and research-grade compressed $H_2$ were supplied by Air Products and Chemicals in cylinders. Syngas (99.99% purity; molar $H_2$/CO ratio of 1:1) was provided by Scott Specialty Gases.

EXAMPLE 1

Solubility of Reactants and Catalysts in $CO_2$-Expanded Liquid

The miscibility of $CO_2$ in the reaction mixtures containing dissolved Rh complexes was investigated in a 50-cm$^3$ Jerguson® view cell, placed in a constant temperature water bath. Details of the apparatus were described in Jin et al., *Homogeneous catalytic hydroformylation of 1-octene in $CO_2$-expanded solvent media*, Chemical Engineering Science, 59 4887-4893 (2004), which is incorporated by reference. The expansion of the liquid mixtures by $CO_2$ is recorded in terms of the relative increase in the liquid volume from the initial state ($CO_2$-free, atmospheric pressure, $P^0$) to the final state ($CO_2$-expanded, equilibrated pressure, P) at the same temperature according to equation 1:

$$V/V_0 = V(T,P)/V(T,P^0)$$

In a typical experiment, the addition of $CO_2$ is continued until either the limit of the operating pressure is reached or a phase separation is observed, with or without catalyst precipitation. The liquid volume corresponding to phase separation is termed as the maximum homogeneous expansion level ("MHEL"). The P-T region below MHEL is employed for performing homogeneous hydroformylation in CXLs while the region above MHEL may be exploited for catalyst precipitation post reaction.

Figure 3:
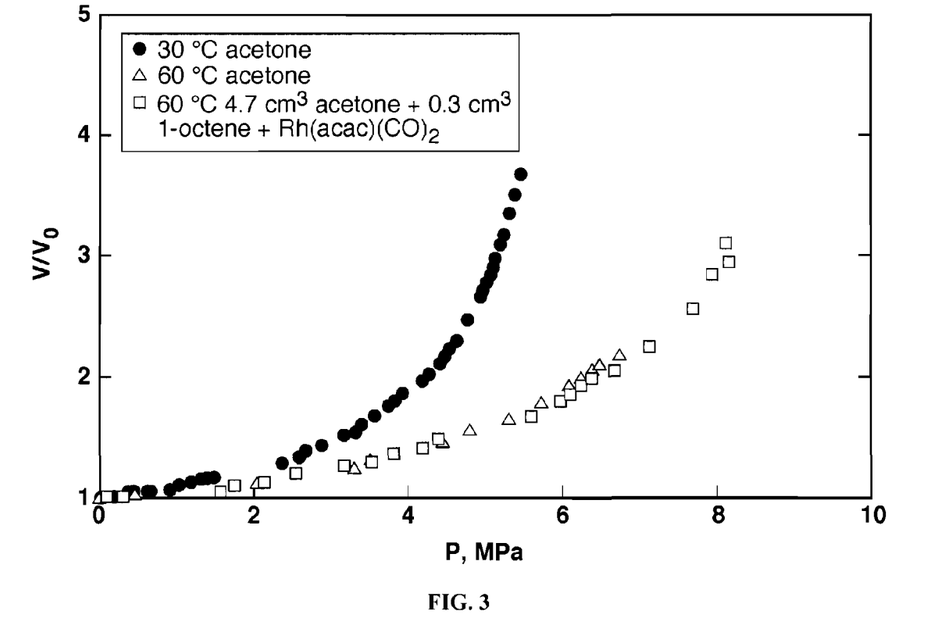
FIG. 3 shows the volumetric expansion of acetone by $CO_2$ at various temperatures.
Figure 4:
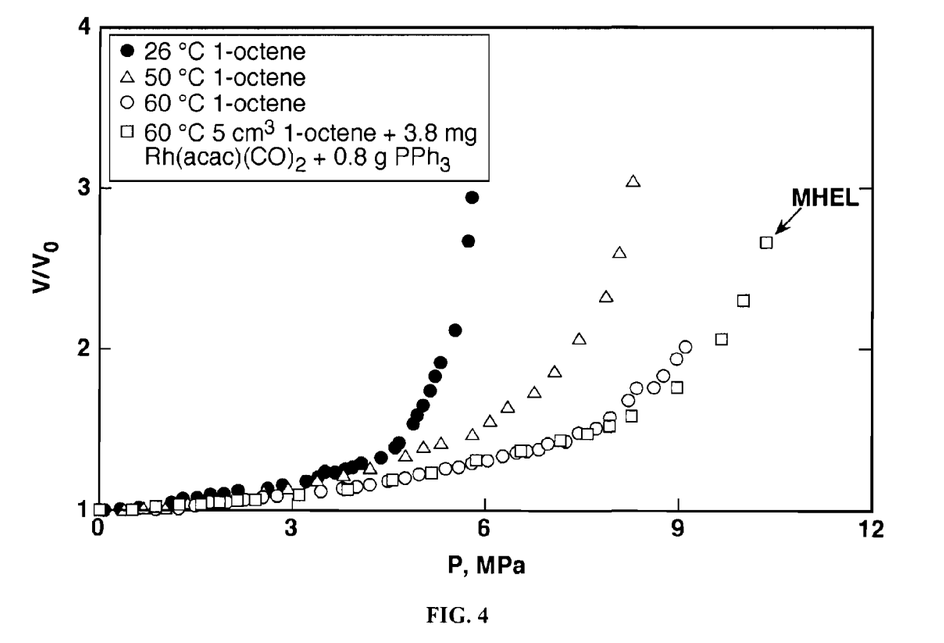
FIG. 4 shows the volumetric expansion of 1-octene by $CO_2$ at various temperatures.

The expansions of acetone and 1-octene at various temperatures, 30-60° C., are presented in FIGS. 3 and 4, respectively. Both solvents demonstrate good miscibility with $CO_2$ at mild pressures (<12 MPa). The volumetric expansions of these liquids in the presence of dissolved Rh catalysts are also compared. No significant variations are observed between the expansions with and without catalysts, because of the relatively dilute catalyst concentrations (about $10^{-3}$ mole/liter). While no catalyst precipitation was observed in $CO_2$-expanded acetone in the range of pressures studied, catalyst precipitation was observed around 9 MPa in $CO_2$-expanded 1-octene at 60° C. Unlike 1-octene, the polar acetone functions as an effective co-solvent for dissolving the Rh complex.

Figure 5:
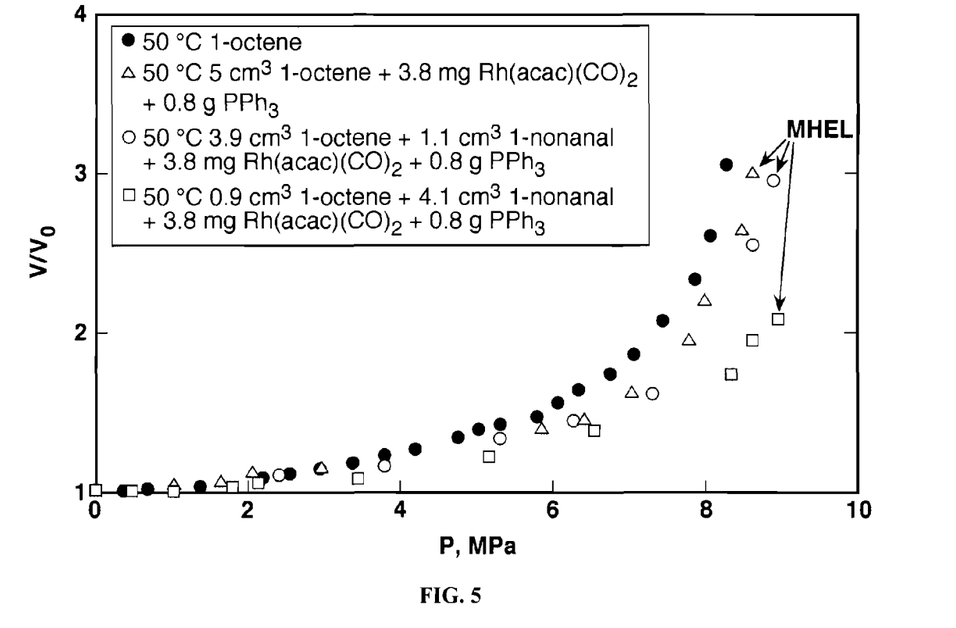
FIG. 5 shows the catalyst solubility in representative hydroformylation reaction mixtures expanded with compressed $CO_2$.

The expansions of several hydroformylation mixtures containing 1-octene, dissolved catalyst [Rh(acac)(CO)$_2$ and PPh$_3$] and nonanals (approximating 0-20% 1-octene conversion to the nonanals) are compared in FIG. 5. In all cases, catalyst precipitation was observed around 9 MPa. These results guide the choice of operating conditions (pressure, temperature, and composition) for the catalyst screening studies, including the level of volumetric expansion at each selected pressure and the range of pressures where 1-octene hydroformylation in CXLs can be performed homogeneously. The observation of MHEL (FIG. 5) also demonstrates the potential of exploiting $CO_2$ as an antisolvent for catalyst recovery.

EXAMPLE 2

Catalyst Screening Experiments

Figure 2:
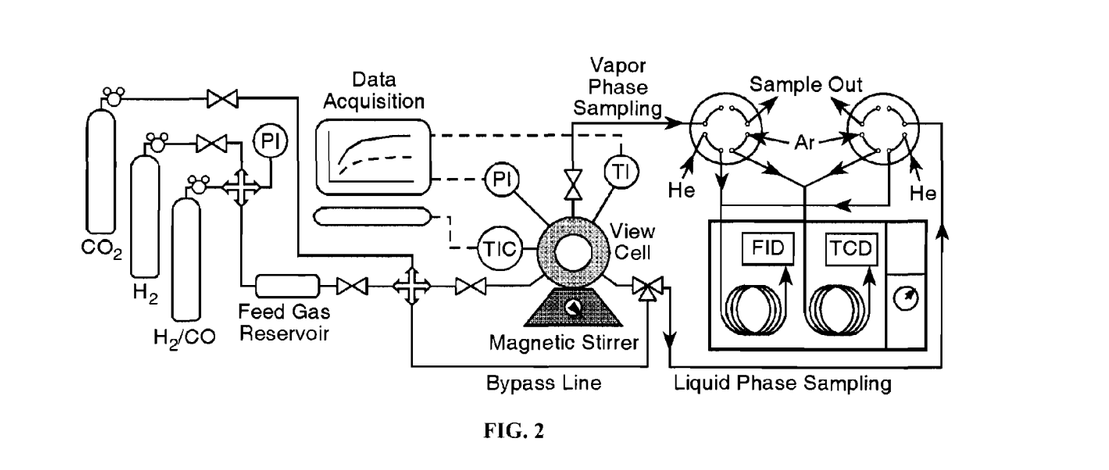
FIG. 2 shows the apparatus schematic for catalyst screening studies discussed in the examples.

The catalytic hydroformylation experiments were performed in fixed-time batch studies using a 15-cm$^3$ 316 stainless steel high-pressure view cell. A schematic of the reactor setup is shown in FIG. 2. Details of the apparatus are discussed in Jin et al., *Homogeneous catalytic hydroformylation of 1-octene in CO$_2$-expanded solvent media*, Chemical Engineering Science, 59 4887-4893 (2004), which is incorporated by reference. Briefly, the cell is fitted with two sapphire windows, which allow visual observations of the phase behavior and the mixing of the reactor contents. Temperature and pressure are monitored and controlled using a data acquisition system (Camile® TG, Argonaut Technologies). In a typical run in $CO_2$-expanded solvents, a liquid mixture containing the substrate, the catalyst, and the organic solvent is preloaded into the reactor and then heated to the reaction temperature, followed by $CO_2$ addition until the desired volume is reached. Syngas is introduced once the system pressure is stabilized, initiating the start of the reaction. Samples are withdrawn from the liquid phase during the experiments and analyzed using an inline gas chromatograph (Varian 3800).

In this example, the reaction temperature was about 30° C. About 2.7 mmol of 1-octene was used as the substrate. The total volume was about 10 cm$^3$, and the volumetric $CO_2$/acetone ratio (v/v) in CXL/acetone runs was about 1. The molar syngas/substrate ratio was about 5, and the molar 1-octene/Rh ratio was about 209.

Table 1 summarizes the results of 1-octene hydroformylation performed in both neat and $CO_2$-expanded acetone solvents with four rhodium-based catalysts: (1) Rh(acac)(CO)$_2$; (2) Rh(acac)[P(OPh)$_3$]$_2$; (3) Rh(acac)(CO)[P(OAr)$_3$]; and (4) a complex formed in situ with molar equivalent amounts of Rh(acac)(CO)$_2$ and the biphephos ligand denominated 1/L1.

TABLE 1

Activity/selectivity of various catalysts in neat and $CO_2$-expanded acetone.

| Media | Catalyst/Ligand | Time (Hour) | Conversion (%) | $S_{aldehyde}$ (%) | n/i |
|---|---|---|---|---|---|
| Acetone | 1 | 20 | 74 | 91.4 | 1.2 |
| | 2 | 6 | 74 | 94.7 | 1.8 |
| | 3 | 6 | 79 | 97.9 | 1.8 |
| | 1/L1 | 6 | 93 | 69.9 | 1.7 |
| CXL/Acetone | 1 | 6 | 73 | 90.3 | 1.3 |
| | 2 | 6 | 91 | 79.5 | 2.1 |
| | 3 | 6 | 97 | 99.2 | 1.9 |
| | 1/L1 | 6 | 97 | 94.0 | 1.7 |

For all four catalysts, 1-octene conversions were greater in $CO_2$-expanded acetone than in neat acetone. With the most active catalyst, the complex formed by Rh(acac)(CO)$_2$ and biphephos ligand, the aldehydes (n+i) selectivity was improved from roughly 70% to 94% in the presence of $CO_2$. The enhanced activity is attributed to increased syngas availability in the $CO_2$-expanded liquid phase, which also promotes hydroformylation over alkene isomerization to internal olefin isomers. It should be noted that the enhanced catalyst performance was achieved with 50% (v/v) replacement of acetone by $CO_2$.

When comparing results in each medium, it is observed that catalysts modified by phosphorous ligands always give higher conversions than the unmodified catalyst, Rh(acac)(CO)$_2$. However, with a PPh$_3$ to metal ("L/Rh") molar ratio of 1, the regioselectivity to the linear aldehyde (n/i ratio) was still several fold lower (n/i<2) than the value preferred in industrial hydroformylation (n/i>5). Table 2 presents the results of 1-octene hydroformylation conducted at molar L/Rh ratios ranging from 103 to 270. A commercial ligand, triphenylphosphine (PPh$_3$) was used and the data were compared to literature values. The reaction temperature was 90° C., and the pressure was 0.6 MPa. About 2.7 mmol of 1-octene was used as the substrate. The total volume was 7 cm$^3$. The molar syngas/substrate ratio was 5, and the molar 1-octene/Rh ratio was 2767 (in toluene) and 2139 (in 1-octene). The reaction was allowed to proceed for about 2.25 hours.

A reasonable agreement was found between the two sets of data. The n/i ratio was increased to 4.7 at higher ligand concentrations. In addition, when the substrate (1-octene) itself was used as solvent medium, both the reaction rates and selectivity were found to be significantly improved. More than a five-fold rate enhancement and an n/i ratio of 13.8 were achieved in the absence of an added organic solvent such as acetone or toluene.

TABLE 2

Hydroformylation of 1-octene at higher Ligand/Rh molar ratios.

| Solvent | Ligand | Ligand/Rh (Molar) | TOF (Hour$^{-1}$) | $S_{aldehydes}$ (%) | n/i |
|---|---|---|---|---|---|
| Toluene[27] | PPh$_3$ | 103 | n/a | 82.0 | 4.6 |
| Toluene | PPh$_3$ | 270 | 161 | 72.8 | 4.7 |
| None | PPh$_3$ | 205 | 887 | 96.7 | 13.8 |

Figure 6:
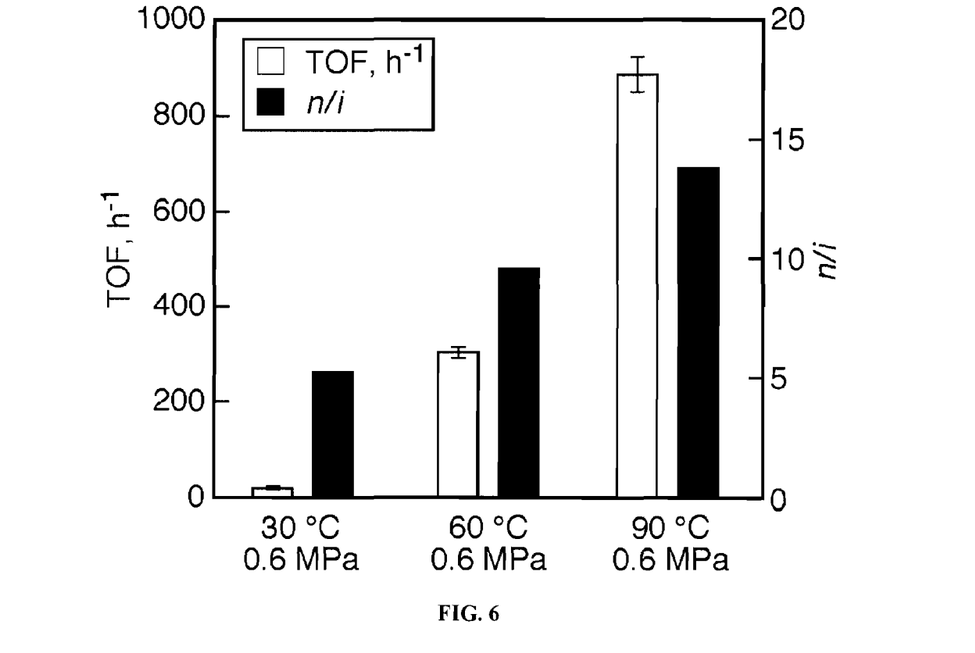
FIG. 6 shows the effect of temperature on activity and product selectivity.

FIG. 6 shows the effects of temperature on 1-octene hydroformylation conducted without added solvent. The performance of Rh(acac)(CO)$_2$ catalyst, modified by PPh$_3$ ligand at L/Rh ratios around 200, is compared at temperatures of 30, 60 and 90° C. Increase in temperature led to higher reaction rates and n/i ratios. The beneficial temperature effect on the linear aldehyde selectivity has been observed by other researchers as well. See Lazzaroni et al., 1-*Hexene rhodium catalyzed hydroformylation at partial substrate conversion: influence of reaction parameters on the chemoselectivity and regioselectivity*, Journal of Molecular Catalysis, 58 75-85 (1990). Literature evidence suggests that octene isomers, the byproducts of 1-octene isomerization, would also hydroformylate and form internal aldehydes, thereby lowering the n/i ratio. An increase in temperature tends to favor the yield of linear aldehyde over 1-octene isomers.

Figure 7:
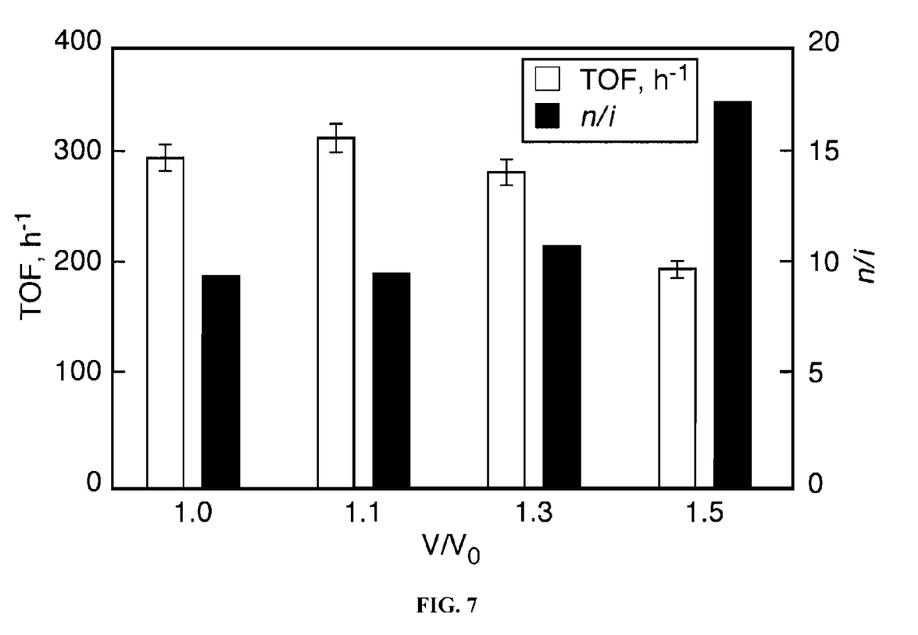
FIG. 7 shows the effects of $CO_2$ addition on TOF and n/i ratio without added solvent.
Figure 8:
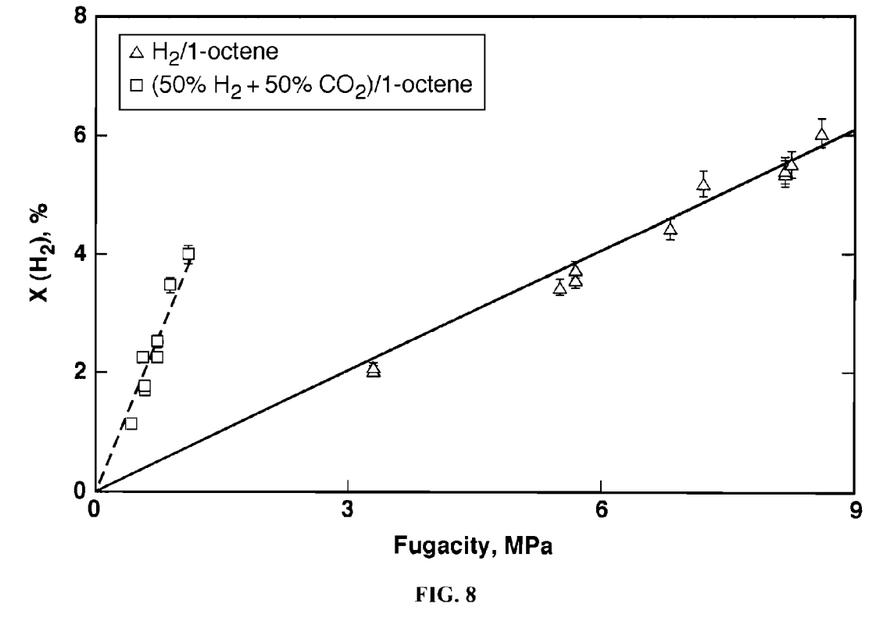
FIG. 8 shows the solubility of $H_2$ in neat and $CO_2$-expanded 1-octene at 60° C.

FIG. 7 presents the effect of $CO_2$ addition at 60° C. The experimental conditions were similar to those in FIG. 6, except that various amounts of $CO_2$ were added to the 1-octene solution in each run. A maximum TOF was observed at a $CO_2$ addition of 10% (by volume). This suggests that although $CO_2$ addition to 1-octene may enhance the syngas availability in the CXL phase, the substrate dilution by $CO_2$ eventually lowers the reaction rates. Measurements of the liquid-phase mole fraction of $H_2$ showed several-fold solubility enhancement in $CO_2$-expanded 1-octene relative to neat 1-octene pressurized with pure $H_2$ at the same pressure (FIG. 8). Remarkably, the $CO_2$ addition was found to continuously improve the n/i ratio. Similar to the temperature effect, increased syngas availability in the liquid phase promotes the hydroformylation route over isomerization, resulting in higher yields of linear product.

Figure 9:
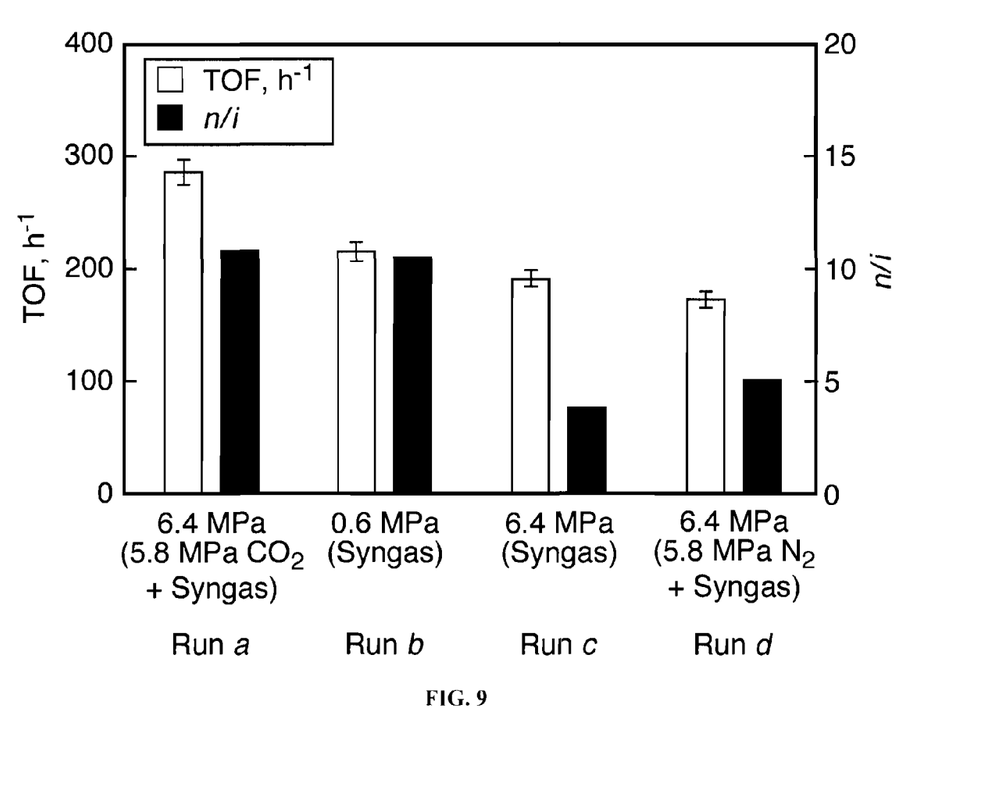
FIG. 9 shows the pressure effects on TOF and n/i ratio. The solvents used are liquid $CO_2$ in run a and n-hexane in runs b-d.

To clarify the $CO_2$ effect, several conversion and selectivity measurements were performed at fixed initial concentrations of the substrate (1-octene) and the catalyst and the batch run-time. The experimental conditions are as follows: (a) a liquid mixture containing 23% $CO_2$ and 77% 1-octene (by volume) is subjected to a total pressure of 6.4 MPa, with the partial pressures of syngas and $CO_2$ being 0.6 and 5.8 MPa, respectively; (b) a liquid mixture with the same volume as in run a but under a total pressure of 0.6 MPa, primarily being the syngas, with the $CO_2$ replaced by a volumetrically equivalent amount of n-hexane, a liquid at ambient pressures and whose polarity is very similar to that of $CO_2$; the conditions in runs c and d are similar to those in run b, except that the vapor phase is comprised of pure syngas (6.4 MPa) in run c, and a mixture of syngas and $N_2$ (partial pressures of syngas and $N_2$ being 0.6 and 5.8 MPa, respectively) in run d. As shown in FIG. 9, the TOFs in $CO_2$-expanded 1-octene at 6.4 MPa (run a) is 33% greater than TOF in n-hexane at 0.6 MPa (run b) with similar n/i ratios in both runs. The TOFs are reduced by roughly a third and the n/i ratio is reduced by more than twofold when $CO_2$ was replaced by either $N_2$ (run d) or syngas (run c). While these results clearly show that the addition of $CO_2$ has a beneficial effect on the TOF and n/i ratio, the inhibition effects due to either $N_2$ or syngas addition are as yet not fully understood. Investigations with a high-pressure IR probe are currently underway to monitor the reacting species in situ, and should provide better mechanistic insights.

Table 3 compares the TOFs, n/i ratio and operating conditions (pressure and temperature) from the current work with those of some existing industrial processes and recently published work that employ supercritical $CO_2$ and ionic liquids as reaction media. See Webb et al., *Continuous flow homogeneous hydroformylation of alkenes using supercritical fluids*, Green Chemistry, 7 373-379 (2005). Clearly, hydroformylation in $CO_2$-expanded octene appears to be promising in terms of both TOF (about 300 h$^{-1}$) and selectivity (about 90%, n/i>10). In addition, the required operating conditions (60° C. and 3.8 MPa) are much milder compared to other processes. Preliminary economic analysis reveals that demonstrating active and easily recyclable catalysts that function effectively in $CO_2$-expanded media is the key to developing commercially viable CXL-based hydroformylation.

TABLE 3

Comparison with commercial processes and other reported work.

| Process | BASF (Co) | Shell (Co/P) | SCF-IL (Rh/P) | SCF (Rh/P) | CXL (Rh/P) |
|---|---|---|---|---|---|
| Substrate | 1-octene | 1-octene | 1-octene | 1-octene | 1-octene |
| P, MPa | 30 | 8 | 20 | 12.5 | 3.8 |
| T, ° C. | 150 | 200 | 100 | 100 | 60 |
| TOF, hour$^{-1}$ | 35 | 20 | 517 | 259 | 316 |
| $S_{aldehyde}$, % | 50 | 80 | 75 | 75 | 89 |

The following references to the extent that they provide exemplary procedural or other details supplementary to those set forth herein, are specifically incorporated herein by reference.

Frohling et al., *Applied homogeneous catalysis with organometallic compounds*, VCH, Weinheim, Germany,: 27-104 (1996).

Garton et al., PCT International Applications, WO 2003/082789 A2.

Marteel et al., *Supported platinum/tin complexes as catalysts for hydroformylation of 1-hexene in supercritical carbon dioxide*, Catalysis Communications, 4 309-314 (2003).

Mukhopadhyay et al., *Encapsulated HRh(CO)—(PPh3)3 in microporous and mesoporous supports: novel heterogeneous catalysts for hydroformylation*, Chemical Materials, 15 1766-1777 (2003).

Yoon et al., *Rh-based olefin hydroformylation catalysts and the change of their catalytic activity depending on the size of immobilizing supporters*, Inorganica Chimica Acta., 345 228-234 (2003).

Dessoudeix et al., *Apatitic tricalcium phosphate as novel smart solids for supported aqueous phase catalysis (SAPC)*, Advanced Synthetic Catalysis, 344 406-412 (2002).

Lu et al., *Hydroformylation reactions with recyclable rhodiumcomplexed dendrimers on a resin*, Journal of American Chemical Society, 125 13126-13131 (2003).

Lopez-Castillo et al., *Evaluation of polymer-supported rhodium catalysts in 1-octene hydroformylation in supercritical carbon dioxide*, Industrial & Engineering Chemistry Research, 42 3893-3899 (2003).

Peng et al., *Aqueous biphasic hydroformylation of higher olefins catalyzed by rhodium complexes with amphiphilic ligands of sulfonated triphenylphosphine analog*, Catalysis Letters, 88 219-225 (2003).

Haumann et al., *Hydroformylation in microemulsions: conversion of an internal long chain alkene into a linear aldehyde using a water soluble cobalt catalyst*, Catalysis Today, 79-80 43-49 (2003).

McCarthy et al., *Catalysis in inverted supercritical CO2/aqueous biphasic media*, Green Chemistry, 4 501-504 (2002).

Webb et al., *Continuous flow hydroformylation of alkenes in supercritical fluid-ionic liquid biphasic systems*, Journal of American Chemical Society, 125 15577-15588 (2003).

Horváth et al., *Facile catalyst separation without water: fluorous biphasic hydroformylation of olefins*, Science, 266 (5182) 72-75 (1994).

Zheng et al., *Thermoregulated phase transfer ligands and catalysis. III. Aqueous/organic two-phase hydroformylation of higher olefins by thermoregulated phase-transfer catalysis*, Catalysis Today, 44 175-182 (1998).

Koch et al., *Rhodium-catalyzed hydroformylation in supercritical carbon dioxide*, Journal of American Chemical Society, 120 13398-13404 (1998).

Palo et al., *Effect of ligand modification on rhodium-catalyzed homogeneous hydroformylation in supercritical carbon dioxide*, Organometallics, 19 81-86 (2000).

Subramaniam et al., *Reaction in supercritical fluids—a review*, Industrial & Engineering Chemistry Process Design and Development, 25 1-12 (1986).

Hert et al., *Enhancement of oxygen and methane solubility in 1-hexyl-3-methylimidazolium bis(trifluoromethylsul-fo-nyl)imide using carbon dioxide*, Chemical Communications, 2603-2605 (2005).

Wei et al., *Autoxidation of 2,6-di-tertbutyl-phenol with cobalt Schiff base catalysts by oxygen in CO2-expanded liquids*, Green Chemistry, 6 387-393 (2004).

Solinas et al., *Enantioselective hydrogenation of imines in ionic liquid/carbon dioxide media*, Journal of American Chemical Society, 126 16142-16147 (2004).

Bezanehtak et al., *Vapor-liquid equilibrium for the carbon dioxide+hydrogen+methanol ternary system*, Journal of Chemical Engineering Data, 49 430-434 (2004).

Xie et al., *Bubble and dew point measurements of the ternary system carbon dioxide+methanol+hydrogen at 313.2 K*, Journal of Chemical Engineering Data, 50 780-783 (2005).

Jin et al., *Exothermic oxidations in supercritical $CO_2$: effects of pressure-tunable heat capacity on adiabatic temperature rise and parametric sensitivity*, Chemical Engineering Science, 58 1897-1901 (2003).

Jin et al., *Homogeneous catalytic hydroformylation of 1-octene in $CO_2$-expanded solvent media*, Chemical Engineering Science, 59 4887-4893 (2004).

Jongsma et al., *Fine tuning of bulky-phosphite modified rhodium catalysts by binding them to copolymers*, Journal of Molecular Catalysis, 83 17-35 (1993).

Billig et al., U.S. Pat. Nos. 4,668,651 (1987) and 4,769,498 (1988).

Pruett et al., *Low-pressure system for producing normal aldehydes by hydroformylation of alpha-olefins*, Journal of Organic Chemistry, 34 327-330 (1969).

Lazzaroni et al., *1-Hexene rhodium catalyzed hydroformylation at partial substrate conversion: influence of reaction parameters on the chemoselectivity and regioselectivity*, Journal of Molecular Catalysis, 58 75-85 (1990).

Webb et al., *Continuous flow homogeneous hydroformylation of alkenes using supercritical fluids*, Green Chemistry, 7 373-379 (2005).

From the foregoing, it will be seen that this invention is one well adapted to attain all ends and objectives herein above set forth, together with the other advantages which are obvious and which are inherent to the invention. Since many possible embodiments may be made of the invention without departing from the scope thereof, it is to be understood that all matters herein set forth or shown in the accompanying drawings are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A method for obtaining a target regioselectivity of linear aldehydes over branched aldehydes during hydroformylation of an olefin comprising
   reacting an olefin substrate with CO and $H_2$ in the presence of a hydroformylation catalyst in a liquid that has been volumetrically expanded with a compressed gas, and
   varying the content of the compressed gas in the liquid in order to obtain said desired target regioselectivity.

2. The method of claim 1 comprising the steps of:
   forming a reaction mixture comprising said olefin substrate and said hydroformylation catalyst in a liquid phase;
   introducing said compressed gas and into said reaction mixture in order to volumetrically expand the reaction mixture; and
   introducing a $H_2$/CO syngas into the reaction mixture;
   whereby said regioselectivity of linear aldehydes is greater than that without said introduction of said compressed gas into said reaction mixture.

3. The method of claim 1 wherein the said olefin substrate is a higher olefin having more than 5 carbons.

4. The method of claim 1 wherein said olefin substrate is a linear olefin.

5. The method of claim 1 wherein said olefin substrate is a branched olefin.

6. The method of claim 1 wherein said olefin substrate has a terminal double bond.

7. The method of claim 1 wherein said olefin substrate has an internal double bond.

8. The method of claim 1 wherein said olefin substrate has more than one double bond.

9. The method of claim 1 wherein said hydroformylation catalyst is a rhodium catalyst.

10. The method of claim 9 wherein said rhodium catalyst is selected from the group consisting of $Rh(acac)(CO)_2$; $Rh(acac)[P(OPh)_3]_2$; $Rh(acac)(CO)[P(OAr)_3]$; and a complex formed of $Rh(acac)(CO)_2$ and a phosphorous-containing ligand.

11. The method of claim 10 wherein said rhodium catalyst comprises a complex of rhodium ("Rh") and ligand ("L") with a molar L/Rh ratio ranging between 1 and 270.

12. The method of claim 11 wherein said molar L/Rh ratio ranges between 103 and 270.

13. The method of claim 1 wherein the reaction mixture further comprises an organic solvent.

14. The method of claim 13 wherein said organic solvent is acetone.

15. The method of claim 13 wherein said organic solvent is also said olefin substrate.

16. The method of claim 1 wherein said compressed gas has a volume fraction in the liquid phase between 10% and 90%.

17. The method of claim 1 wherein said compressed gas is dense carbon dioxide.

18. The method of claim 1 wherein said target regioselectivity is greater than 10.

19. The method of claim 1 wherein said reaction mixture is maintained at a temperature between 30° C. and 90° C.

20. The method of claim 1 wherein said reaction mixture is maintained at a pressure less than 12 MPa.

21. The method of claim 20 wherein said pressure is between about 4 to 6 MPa.

22. A method for obtaining a target chemoselectivity of aldehydes during hydroformylation of an olefin comprising
reacting an olefin substrate with CO and $H_2$ in the presence of a hydroformylation catalyst in a liquid that has been volumetrically expanded with a compressed gas, and
varying the content of the compressed gas in the liquid in order to obtain said desired target chemoselectivity.

23. The method of claim 22 wherein the said olefin substrate is a higher olefin having more than 5 carbons.

24. The method of claim 22 wherein said olefin substrate is a linear olefin.

25. The method of claim 22 wherein said olefin substrate is a branched olefin.

26. The method of claim 22 wherein said olefin substrate has a terminal double bond.

27. The method of claim 22 wherein said olefin substrate has an internal double bond.

28. The method of claim 22 wherein said olefin substrate has more than one double bond.

29. The method of claim 22 wherein said hydroformylation catalyst is a rhodium catalyst.

30. The method of claim 29 wherein said rhodium catalyst is selected from the group consisting of $Rh(acac)(CO)_2$; $Rh(acac)[P(OPh)_3]_2$; $Rh(acac)(CO)[P(OAr)_3]$; and a complex formed of $Rh(acac)(CO)_2$ and a phosphorous-containing ligand.

31. The method of claim 30 wherein said rhodium catalyst comprises a complex of rhodium ("Rh") and ligand ("L") with a molar L/Rh ratio ranging between 1 and 270.

32. The method of claim 31 wherein said molar L/Rh ratio ranges between 103 and 270.

33. The method of claim 22 wherein the reaction mixture further comprises an organic solvent.

34. The method of claim 33 wherein said organic solvent is acetone.

35. The method of claim 33 wherein said organic solvent is also said olefin substrate.

36. The method of claim 22 wherein said compressed gas has a volume fraction in the liquid phase between 10% and 90%.

37. The method of claim 22 wherein said compressed gas is dense carbon dioxide.

38. The method of claim 22 wherein said regioselectivity is greater than 10.

39. The method of claim 22 wherein said reaction mixture is maintained at a temperature between 30° C. and 90° C.

40. The method of claim 22 wherein said reaction mixture is maintained at a pressure less than 12 MPa.

* * * * *